United States Patent [19]

Phillips et al.

[11] Patent Number: 4,569,674
[45] Date of Patent: Feb. 11, 1986

[54] CONTINUOUS VACUUM WOUND DRAINAGE SYSTEM

[75] Inventors: Earl G. Phillips, Kalamazoo; Robert W. Insalaco, Climax; William M. Booth, III, Paw Paw, all of Mich.

[73] Assignee: Stryker Corporation, Kalamazoo, Mich.

[21] Appl. No.: 404,791

[22] Filed: Aug. 3, 1982

[51] Int. Cl.$^4$ .............................................. A61M 1/00
[52] U.S. Cl. ................................... 604/119; 604/319; 604/322
[58] Field of Search ............... 604/118, 119, 120, 126, 604/127, 122, 131, 317–320, 322, 323, 326, 327, 47, 73, 48, 50, 4–6; 128/760, 762, 5, 6; 417/9

[56] References Cited

U.S. PATENT DOCUMENTS

| | | | |
|---|---|---|---|
| 3,363,626 | 1/1968 | Bidwell et al. | 604/151 |
| 3,545,440 | 12/1970 | Mishkin et al. | 604/321 |
| 3,572,340 | 3/1971 | Lloyd et al. | 604/133 |
| 3,675,653 | 7/1972 | Crawley et al. | 604/120 |
| 3,993,062 | 11/1976 | Jess | 604/126 |
| 4,178,932 | 12/1979 | Ryder et al. | 604/118 |
| 4,184,510 | 1/1980 | Murry et al. | 604/30 |
| 4,256,109 | 3/1981 | Nichols | 604/320 |
| 4,261,360 | 4/1981 | Perez | 604/118 |
| 4,296,748 | 10/1981 | Kurtz et al. | 128/762 |
| 4,306,558 | 12/1981 | Kurtz et al. | 604/73 |
| 4,345,342 | 8/1982 | Saito | 128/762 |
| 4,392,858 | 7/1983 | George et al. | 604/126 |
| 4,395,258 | 7/1983 | Wang et al. | 604/119 |

FOREIGN PATENT DOCUMENTS 2058227 4/1981 United Kingdom .

OTHER PUBLICATIONS

WO80/02706 PCT Goldberg et al. 12/80.

Primary Examiner—Lee S. Cohen
Assistant Examiner—Steven Falk
Attorney, Agent, or Firm—Flynn, Thiel, Boutell & Tanis

[57] ABSTRACT

A continuous vacuum drainage system for wound drainage. A base unit has apparatus responsive to releasable attachment thereto of a drain reservoir for evacuating the reservoir to a subatmospheric pressure in a predetermined range. The drain reservoir is continuously operable before, during and after release from the base unit for uninterrupted suction draining of a wound.

32 Claims, 15 Drawing Figures

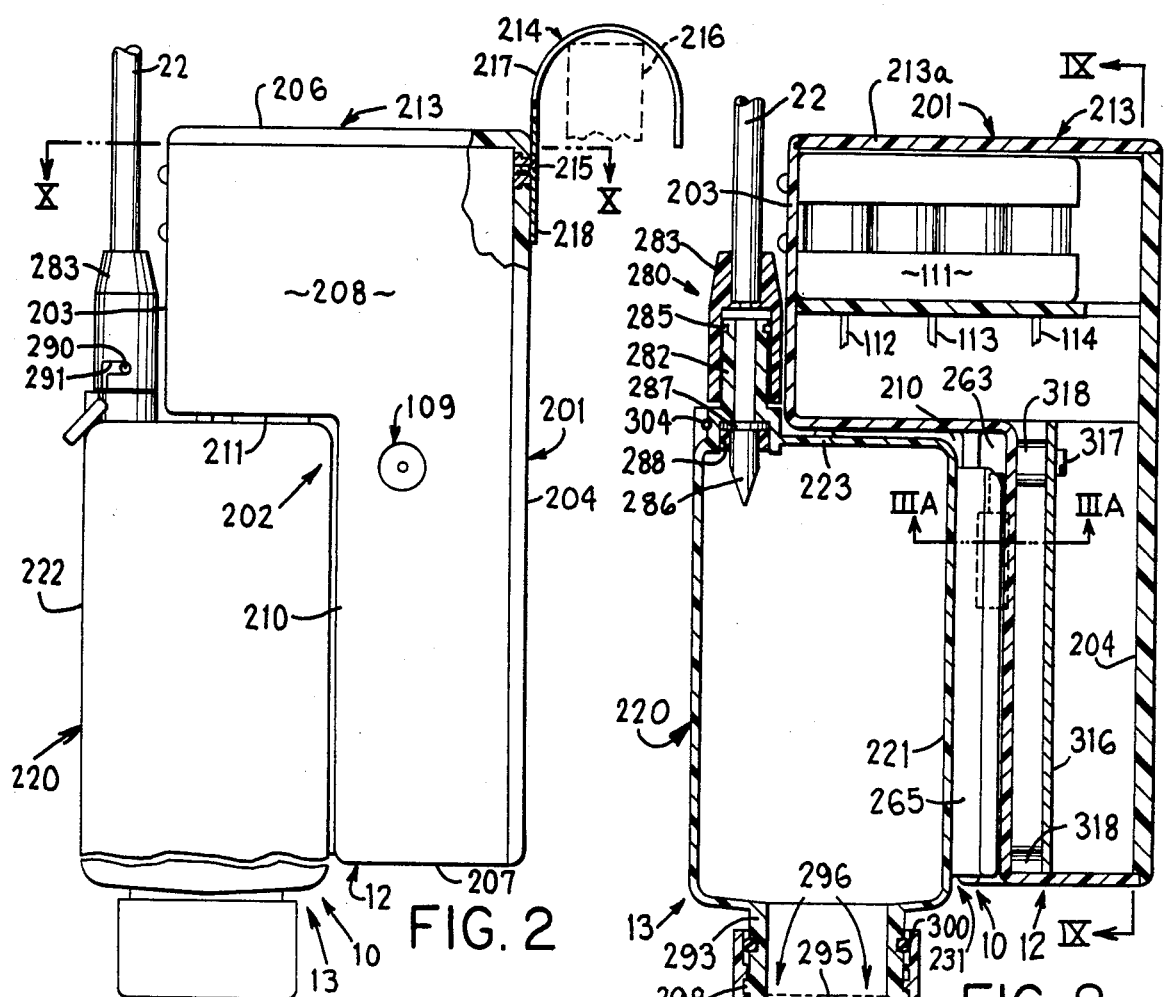
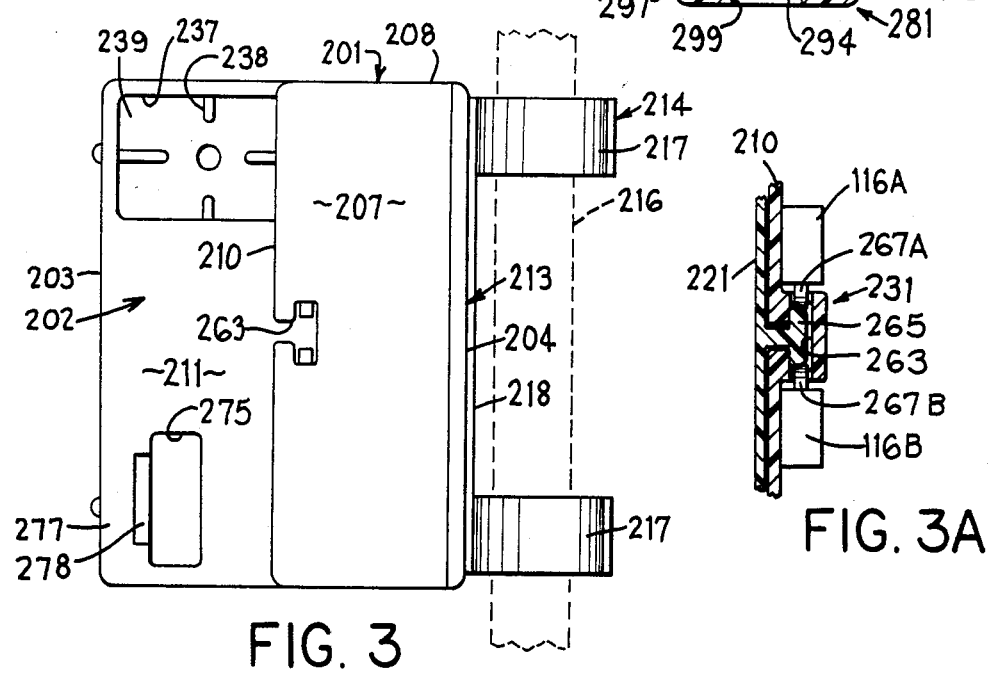

CONTINUOUS VACUUM WOUND DRAINAGE SYSTEM

FIELD OF THE INVENTION

This invention relates to a vacuum drainage system for wounds, and more particularly to such system having a reservoir connectible to the wound for receiving drainage fluid therefrom and apparatus for applying a negative pressure to the reservoir.

BACKGROUND OF THE INVENTION

It has long been known to drain unwanted liquid from a wound by means of a tube connected to a closed container, the interior of which is under a partial vacuum, that is, a subatmospheric or negative pressure.

In one type of prior apparatus, the drainage container is provided with a wall or walls manually deflectable inward for reducing the effective volume within the container and resilient means for oppositely deflecting such wall or walls to expand the internal volume of the container and thereby establish a negative pressure therein for drawing liquid from the wound. In some instances, these units have been made compact and light weight enough to be secured to and carried by an ambulatory patient, for example after surgery to continue drainage of the healing wound. One example is disclosed by Lloyd U.S. Pat. No. 3,572,340. However, such devices typically do not provide precise control of maximum negative pressure since the degree of inward deflection may vary widely among different users or may not be clearly or reliably related to developed maximum negative pressure. This risks excessive negative pressure when the device is used in connection with a slow draining wound in relatively delicate tissue or ineffectual suction when the device is used to drain thicker liquids from a wound in relatively heavy muscle tissue. Moreover, such prior devices are operable only for a relatively short time in that the device may pass quickly through the desired range of negative pressures prior to completely filling with drained liquid material and hence require frequent changing or emptying, resulting in waste of limited available nursing time.

On the other hand, prior drainage devices of another kind may more closely maintain negative pressure within a drain container in a relatively narrow negative pressure range and may be capable of continuous operation over a relatively long time without need to deform the container or otherwise manually reactivate the negative pressure source. One example is shown in Crowley U.S. Pat. No. 3,675,653. However, systems of this kind have generally been relatively bulky and hence have confined the patient to close proximity to a stationary vacuum pump and control.

Accordingly, prior systems of which we are aware have not been satisfactory for providing precisely controlled, continuous vacuum wound drainage for a patient starting in the operating room with closing of a surgical procedure, and continuing during transport of the patient from operating room to recovery room, while in the recovery room, during transfer to the hospital room, while in his hospital bed, and during subsequent travel by wheelchair or on foot around or out of his hospital room.

Accordingly, the objects and purposes of this invention include provision of a continuous vacuum wound drainage system intended to overcome disadvantages such as those set forth above.

The objects and purposes of this invention are met by providing a continuous vacuum drainage system for wound drainage including a drain reservoir, a base unit having means responsive to releasable attachment thereto of such a drain reservoir for evacuating such reservoir to a subatmospheric pressure in a predetermined range, and wherein the drain reservoir has means continuously operable before, during and after release from the base unit for uninterrupted suction draining of a wound.

Other objects and purposes of this invention will be apparent to persons acquainted with apparatus of this general type upon reading the following specification and inspecting the accompanying drawings.

BRIEF DESCRIPTION OF THE DRAWINGS

FIG. 2 is a partially broken side view of the apparatus of FIG. 1.

FIG. 3 is a bottom view of the apparatus of FIG. 2.

FIG. 3A is a fragmentary sectional view substantially as taken on the line IIIA—IIIA of FIG. 8 hereafter described.

FIG. 8 is a central cross-sectional view substantially as taken on line VIII—VIII of FIG. 1.

FIG. 11A is a block diagram of the power supply portion of the control circuitry for applying DC operating potential to the FIG. 11 apparatus.

DETAILED DESCRIPTION

Figure 1:
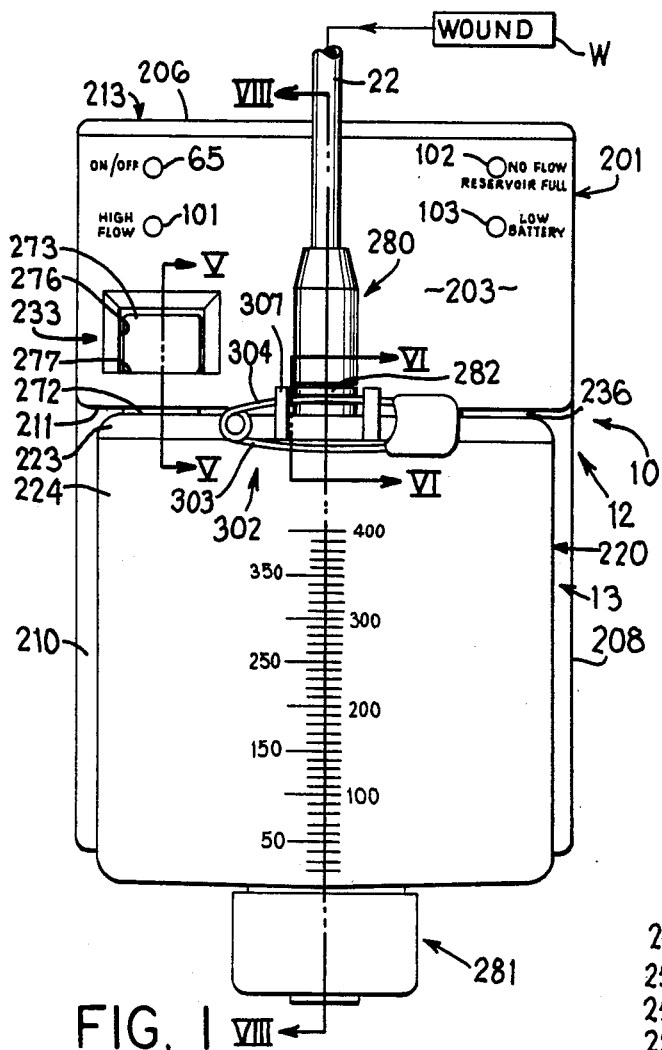
FIG. 1 is a front view of a continuous vacuum wound drainage system embodying the invention, with the reservoir installed in a position of use on the base unit.

FIGS. 1 and 2 disclose a continuous vacuum drainage system 10 for draining of a closed wound. The system 10 includes a portable drain reservoir 13 and a base unit 12 to which the reservoir is releasably securable for partial evacuation to a subatmospheric (negative) pressure. A wound drain tube 22 is used to connect the reservoir 13 to a wound W to be drained. The reservoir 13 is disconnectible from the base unit 12 without such disconnection impairing the negative pressure within the reservoir. Thus, the reservoir 13 can be used for vacuum wound drainage both while connected with the base unit 12 as shown in FIGS. 1 and 2 as well as after disconnection from the base unit, thus permitting the reservoir to be carried by the patient or on a mobile patient support (not shown) to locations remote from the base unit 12.

The base unit 12 comprises a housing 201 (FIGS. 1, 2 and 3) which in the preferred embodiment housing 201 has a forwardly and downwardly facing recess 202 (FIGS. 2 and 3) into which the reservoir 13 is insertable. The housing 201 is conveniently rectilinear, except for the recess 202, and comprises front and back walls 203 and 204, top and bottom walls 206 and 207 and side walls 208. The recess 202 has forward and downward facing walls 210 and 211. The top and rear walls 206 and 204 conveniently together form a cover 213 (FIGS. 2 and 8) removable from the remainder of the housing to allow access to the interior. Cover 213 is releasably fixed to the remainder of the housing 201 by any conventional means, such as screws, not shown. Housing 201 is preferably of a molded plastics material.

An attachment bracket 214 (FIG. 2) is fixed to the housing 201, as by screws 215 for removably supporting the housing on a support indicated in broken lines at 216, for example a fixed support in a hospital or operating room, or a rail or other part on a semi-mobile or mobile patient carrier, such as a hospital bed, gurney, or wheelchair. Bracket 214 preferably comprises a pair of downwardly opening hooks 217 spaced at opposite ends of and extending upward from a mounting plate 218 secured by the screws 215 to the upper edge of housing back 204 to pendantly support the housing 201.

The drain reservoir 13 comprises a hollow bottle 220 (FIGS. 1, 4 and 8) having a back wall 221 complimentary to the forwardly facing recess wall 210 and hence flat in the embodiment shown. The bottle 220 is conveniently approximately rectilinear and is received in the housing recess 202 with its front wall 222 spaced forwardly from the front wall 203 of the housing, as seen in FIG. 2, to provide room for the wound drain tube 22 and means (hereinafter described) connecting same to the bottle.

The reservoir 13 may be manufactured in any convenient manner. To simplify manufacture and permit parts thereof, such as described hereafter with respect to FIG. 7, to be provided within the bottle 220, the bottle 220 may be assembled from a separate top 223 fixedly sealed to a cup-shaped bottom 224, as by the overlapped joint 226 (indicated only at the left in FIG. 7 but extending circumferentially around the top 223 and bottom 224) fixedly as by adhesive or heat.

Insertion of the reservoir 13 into the recess 202 of housing 12 interengages the two by means of a vacuum connection assembly 229 (FIG. 7) through which the base unit provides the reservoir with a negative pressure, and by means of mounting structure for supporting the reservoir on the housing. Such mounting structure includes a single motion guide assembly 231 (FIGS. 3A and 8) for guiding the reservoir properly into position on the housing, and a latch assembly 233 (FIGS. 1 and 5) for releasably fixing the reservoir in supported relation on said housing. In the preferred embodiment shown, the vacuum connection assembly 229, guide assembly 231 and latch assembly 233 are all arranged for straight line upward insertion of the reservoir 13 into the recess 202 of the base unit 12.

Figure 9:
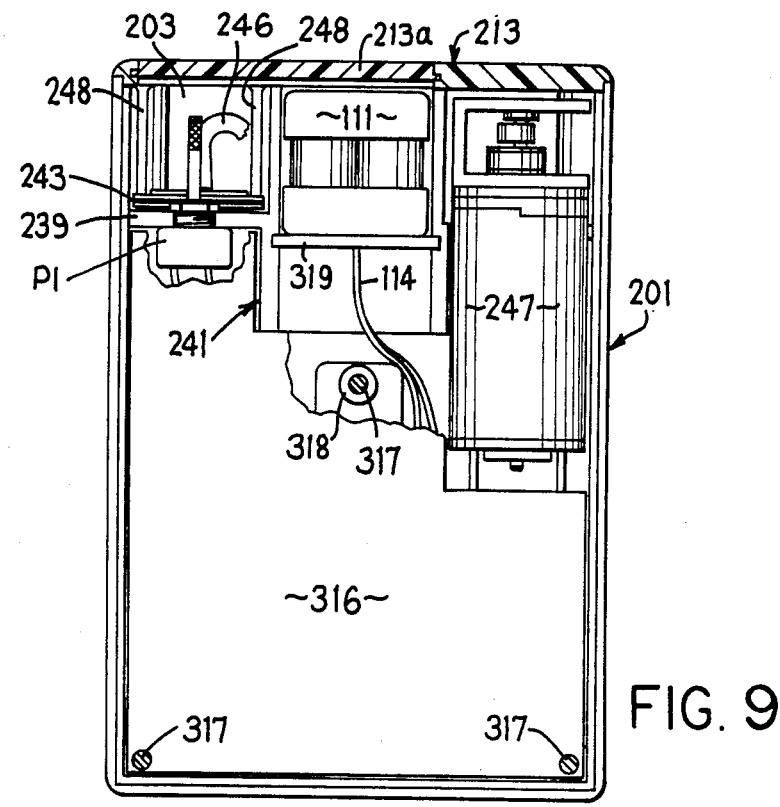
FIG. 9 is a partially broken sectional view substantially taken on the line IX—IX of FIG. 8.
Figure 10:
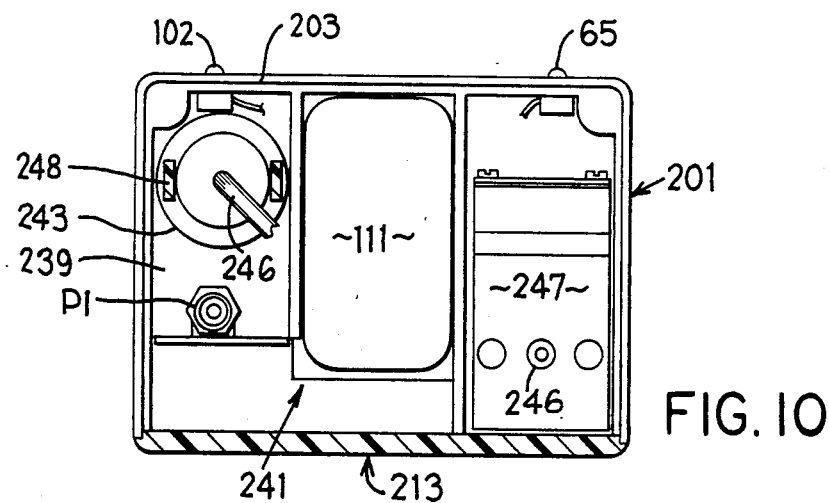
FIG. 10 is a partially broken top view substantially taken on the line X—X of FIG. 2.

The vacuum connection assembly 229 (FIG. 7) includes a hollow cylindrical boss 236 extending upward from the right (FIGS. 1 and 4) rear corner portion of the bottle top 223. A pocket 237 (FIGS. 3 and 7) opens downward through the downward facing wall 211 of the housing into recess 202 and has taper-ended vertical guide ribs 238 fixed therein to snugly guide the upper end of the boss 236 of the bottle upward against, or substantially against, the upper end 239 of the pocket 237, and such that the top 223 of the bottle lies just beneath the overhanging, downwardly facing wall 211 of the housing. The pocket upper end 239 here defines a shelf which, conveniently, is formed as part of a shelf assembly 241 (FIGS. 9 and 10) preferably molded integrally with the front wall 203 of the housing 201, as seen in FIGS. 9 and 10.

A commercially available, disklike, hydrophobic filter unit 243 (FIG. 7) rests atop the shelf 239 and has an upwardly protruding hollow stem 244 connected through a vacuum hose 246 to a motor driven vacuum pump unit 247 (FIGS. 9 and 10) preferably fixed on a further portion of the shelf assembly 241 within the housing. The filter unit 243 is releasably held on the shelf 239 by any convenient means, here by a pair of legs 248 fixedly depending from the removable housing top wall.

Figure 7:
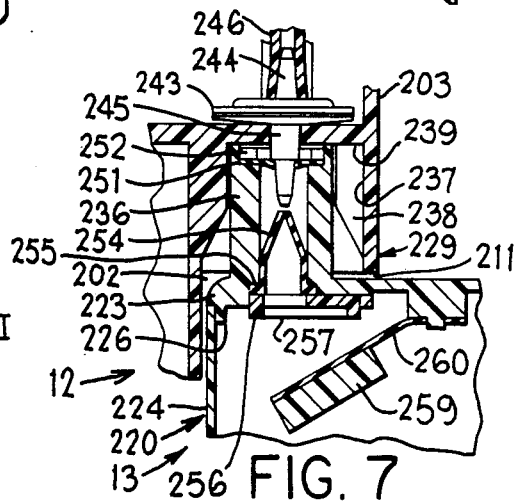
FIG. 7 is a fragmentary sectional view of the vacuum connection assembly substantially as taken on the line VII—VII of FIG. 4.

The filter unit 243 also has a depending hollow stem 245 (FIG. 7). Stem 245 extends downward through an opening in the housing shelf 239 and thence sealingly through an annular resilient membrane 251 (here of latex or the like) held in the stepped upper end of the boss 236 by a conventional resilient friction ring 252 to seal the vacuum connection from the interior of the hollow boss 236, through the filter unit 243 to the vacuum pump 247.

A one-way valve 254 in the hollow boss 236 beneath stem 245 in the preferred embodiment shown is of the commercially available reflux, or "duck-bill" type. The one-way valve 254 is oriented for evacuation of gas upward from the reservoir by the vacuum pump unit 247 but closes upon shutting off or disconnection of the vacuum pump for preventing backflow of air or the like therethrough into the bottle 220. A conventional duck-bill valve 254 has an upstanding tubular central portion, opposite sides of which are pre-biased to flatten and converge toward the top of the valve to form a slit normally resiliently closed to block downward flow therethrough but resiliently openable to allow upward flow therethrough. The bottom of the duck-bill valve 254 is flanged at 255 to seat in the stepped bottom of the boss 236. A perforated retainer 256 is fixed, as by adhesive bonding, beneath the top 223 of the bottle to retain the valve 254, normally to allow upward gas flow from the bottle interior through the valve 254 to the vacuum pump, and also to provide a downward facing seat 257. A float valve 259 comprises a floating body (for example of closed pore, rigid plastic foam) hinged by a flexible leaf 260 of plastic film on the underside of the bottle top 223, to lift up and seal against the perforated retainer 256 and prevent overflow should liquid in the bottle rise to near the top.

Downward movement of the reservoir 13 out of engagement with the base unit 12 pulls the boss 236 out of the pocket 237 and thereby removes the hollow stem 245 from the membrane 251 to disconnect the vacuum pump 247 from the bottle 220. However, the partial vacuum, or negative pressure, in the bottle remains due to closure of the one-way valve 254.

Figure 4:
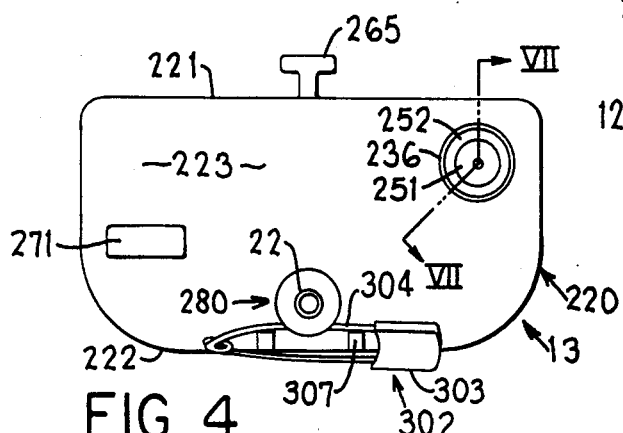
FIG. 4 is a top view of the reservoir of FIG. 1.

The guide assembly 231 (FIGS. 3A and 8) comprises an undercut slot 263 formed, as by molding, in the forwardly facing wall 210 of the housing recess 202. The slot 263 is preferably centrally located on the forwardly facing wall 210 and extends vertically from top to bottom thereof. A T-cross-section rail is fixed, preferably by molding, to the back wall 221 of the bottle 220 as seen in FIG. 4, and is snugly but upwardly slidably receivable in the undercut slot 263 of the housing to guide the bottle 220 upward into the housing recess 202 and guide the boss 236 upward into the pocket 237. The T-rail 265 preferably extends vertically substantially the full height of the bottle 220 and is preferably centered laterally on the back wall 221 thereof. The T-rail 265 and the surfaces defining the undercut slot 263 may be chamfered at their respective upper and lower ends to facilitate entry of the top of the T-rail into the bottom of the undercut slot.

To sense the insertion of the reservoir 13 into the base unit 12 and to control application of electric power to components (such as the vacuum pump 247) within the housing 201, a power switch unit 116 (FIG. 3A) here comprises individual on-off switches 116A and 116B actuable to a conductive state by insertion of the reservoir 13 into the base unit 12. In the embodiment shown, switches 116A and 116B are fixed on the interior side of the forwardly facing recess wall 210 near the top thereof and have respective actuators 267A and 267B extending through openings in the housing wall into the undercut slot 263 for displacement by the top of the T-rail 265 during the last of its rise along the undercut slot 263. Positioning of the switch actuators 267A and 267B within the undercut slot 263 minimizes risk of switch actuation by tampering or unintended touching, when no reservoir is in place on the housing. Suitable seal means, not shown, may be provided where the mechanical switch actuators 267A and 267B protrude through the housing wall into the undercut slot 263.

While mechanically actuated switches are shown for illustrative purposes, switches of other types may be used, for example, proximity switches, such as magnetically operated reed switches actuated by magnetized means on the T-rail 265, or optical or other nonmechanically operated switches. Use of a nonmechanically operated switch at 116A and 116B eliminates the need for any perforation through the wall of the housing and hence any need for a seal thereat.

Figure 5:
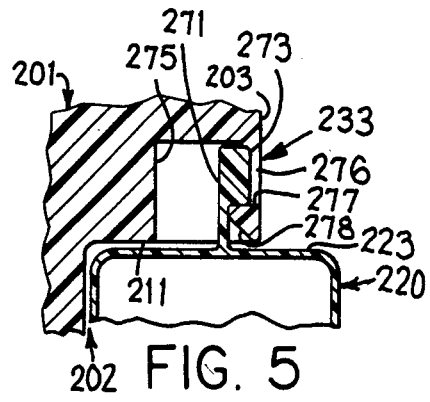
FIG. 5 is a diagrammatic cross-sectional view substantially taken on the line V—V of FIG. 1.

The latch assembly 233 (FIGS. 1, 3 and 5) includes a manually releasable snap-type structure pendantly supporting the bottle 220 snugly beneath the downward facing wall 211 of the housing recess 202. The latch assembly 233 here includes an upstanding deflectable member 271 generally of L-shaped cross section as seen in elevation in FIG. 5. The member 271 has a resiliently rearwardly deflectable first leg 272 upstanding from and fixed (preferably by integral molding therewith) to the top 223 of bottle 220. The deflectable leg 272 is thin from front to rear as seen in FIG. 5 and substantially wider from side to side as seen in FIG. 1, to permit rearward deflection of the top of the member 271 rearwardly. The top leg 273 extends forwardly from the top of deflectable leg 272 and is considerably taller and wider than its front-to-rear thickness. The deflectable member 271 is spaced along the top of the bottle from both the boss 236 and the axis of drain tube 22 as seen in FIG. 4.

An opening 275 opens through the downward facing wall 211 of the housing 201 near the housing front wall 203. The top portion of the opening 275 opens forwardly through the housing front wall 203 to form a finger access port 276. The bottom of port 276 is closed by a transversely extending portion of the housing front wall, namely a ledge 277 on the flat top of which the forward facing top leg 273 of the member 271 rests to latch the bottle 220 in pendantly supported relation on the housing 201. Inserting a human finger through the port 276 shifts top leg 273 rearwardly in the opening 275 and off the ledge 277, thereby unlatching the bottle 220 and allowing it to drop from the housing 221. Upward insertion and latching of the bottle 220 with respect to the housing 201 is facilitated by a sloped camming surface 278 on the underside of the ledge 277 which rearwardly deflects the top leg 273 upon upward movement of the deflectable member 271 into the opening 275, until the bottle 220 has substantially completed its upward motion into the housing recess 202, at which point the upper leg 273 moves fully upward past the ledge 277 and snaps forward, due to its inherent resiliency, into its FIG. 5 latching position.

Turning now to portions of the reservoir 13 engaged by liquid drained from wound W, same include a wound drain port 280 (FIGS. 1 and 8) at which the wound drain tube 22 is releasably connectible to the top of the bottle 220, and a bottle emptying port 281 at the bottom of the bottle for emptying of liquid collected from the wound.

The wound drain port 280 comprises an internally and externally stepped hollow boss 282 (FIG. 8) fixed, and preferably integrally molded, in upstanding relation on the front portion of the top 223 of bottle 220, ahead of the front wall 203 of the housing 201. The wound drainage tube 22 terminates in a sleeve 283 for removable telescoping over the upstanding boss 282 on the bottle. The sleeve 282, near its upper end, has an annular groove for receiving an O-ring seal, or the like, at 285 for sealing against leakage of liquid from the wound between the sleeve and boss. A one-way valve 286, here of the reflux or "duck-bill" type used at 254 in the vacuum connection assembly 229 above discussed, extends pendantly into the bottle 220 with its upper end flange 287 removably fixed in the stepped lower end of the boss 282 by a resilient friction retainer ring 288. The one-way valve 286 permits in-flow of liquid from the wound through tube 22 and the central through-bore of hollow boss 282, but precludes reverse flow from the interior of bottle 220, to preclude contamination of the wound.

To releasably secure the wound drain tube 22 by its sleeve 283 to the upstanding hollow boss 282 on the bottle, a releasable latch 289 is provided. The latch 289 here is of bayonet type and comprises a pin 290 protruding radially from the boss 282 for entering an L-shaped slot 291 at the bottom of sleeve 283 (FIG. 2). Latching is accomplished by downward movement of the tube 22 and sleeve 283 to enter the pin 290 in the vertical lower leg of the slot 291, whereafter rotation of the sleeve 283 and tube 22 locates the pin 290 at the blind end of the horizontal leg of the L-shaped slot 291 to axially fix the sleeve 283 and tube 22 to the bottle. The tube 22 and sleeve 283 are releasable from the bottle by reversal of the rotation and axial latching movements above described.

The emptying port 281 comprises a short hollow boss 293, of wider diameter than bosses 236 and 282 above described and depending from the bottom of the bottle 220. At the open bottom of the boss 293, a coaxial, downwardly tapering valve member 294 (FIG. 8) is fixed by a diametrally extending crossbar 295, preferably integrally molded therewith and with the boss 293. The boss 293 is preferably integrally molded with the bottle 220. The valve member 294 is of lesser diameter than the interior bore of the boss 293 to provide therebetween a generally annular liquid out-flow space 296 spanned by the crossbar 295. A cup-shaped cap 297 is upwardly threaded at 298 onto the depending boss 293, and has a central out-flow opening 299 complementary to the valve member 294. Thus, with the cap 297 tightly threaded on the boss 293, the valve member 294 seals the central opening 299 of the cap to prevent out-flow of fluids from the bottom of the bottle. On the other hand, when the cap 297 is partially loosened, the valve member 294 is loose in the central opening 299 in the cap and liquid can flow outward through the central opening 299 of the cap to drain the bottle 220. If desired, the cap 297 may be entirely removable from the boss 293, as for cleaning. The boss 293, above the threads 298 therein, is here provided with an annular groove seating a suitable seal, such as an O-ring seal 300, for snugly and sealingly engaging a recess in the open upper end of the cap 297.

Figure 6:
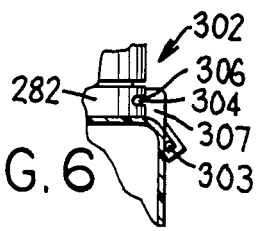
FIG. 6 is a fragmentary side view of the upper forward portion of the reservoir substantially taken on the line VI—VI of FIG. 1.

To move the patient from the location of the base unit 12 for a time, the reservoir 13 can be removed from the base unit, while still holding a negative pressure and being connected to the wound W on the patient, to travel with the patient. To this end, the reservoir 13 includes an attachment unit 302 (FIGS. 1, 4 and 6) securable to the patient or to a mobile patient support such as a wheelchair. In the embodiment shown, the attachment unit 302 comprises a conventional large safety pin 303 having a fixed leg and a movable leg, the fixed leg 304 being removably fixed to the front upper edge portion of the bottle 220. More particularly, the fixed leg 304 is held in snap-fit relation in a lateral groove 306 in the front face of the boss 282 by a pair of upstanding fingers 307 preferably molded integrally with the top 223 of the bottle 220. The rear edges of the fingers 307 define a plane substantially tangent to the front of the boss 282 and the fingers 307 are spaced laterally on opposite sides of the boss 282. The fingers 307 hold the fixed leg of the pin securely in the groove 306 for pinning of the reservoir to the patient's clothing, blanket, or the like. The resilience of the wire of the fixed leg 304 of the pin and, if desired, some resilience in the fingers 307, permits intended forceful dislodgment from, or installation on, the bottle 220 of the safety pin 303.

When the reservoir 13 is removed from the base unit 12, an existing negative pressure within the bottle 220 will be maintained by closure of the one-way valve 254 (FIG. 7) to continue drawing out liquids from the wound W through tube 22 into the bottle 220. If desired, and particularly to avoid accidental depositing of foreign matter in the interior of the hollow boss 236, the upper end thereof may be formed with an outward facing annular groove 309 (FIG. 7A) for receiving, here by snap-fit connection, a removable cap 310. The fit between the internal annular lip 311 of the cap 310 and the groove 309 on boss 236 establishes a secondary vacuum seal in case one-way valve 254 unexpectedly leaks and also positively prevents liquid leakage from the bottle if the latter overturns or is jarred while upside down.

Figure 11:
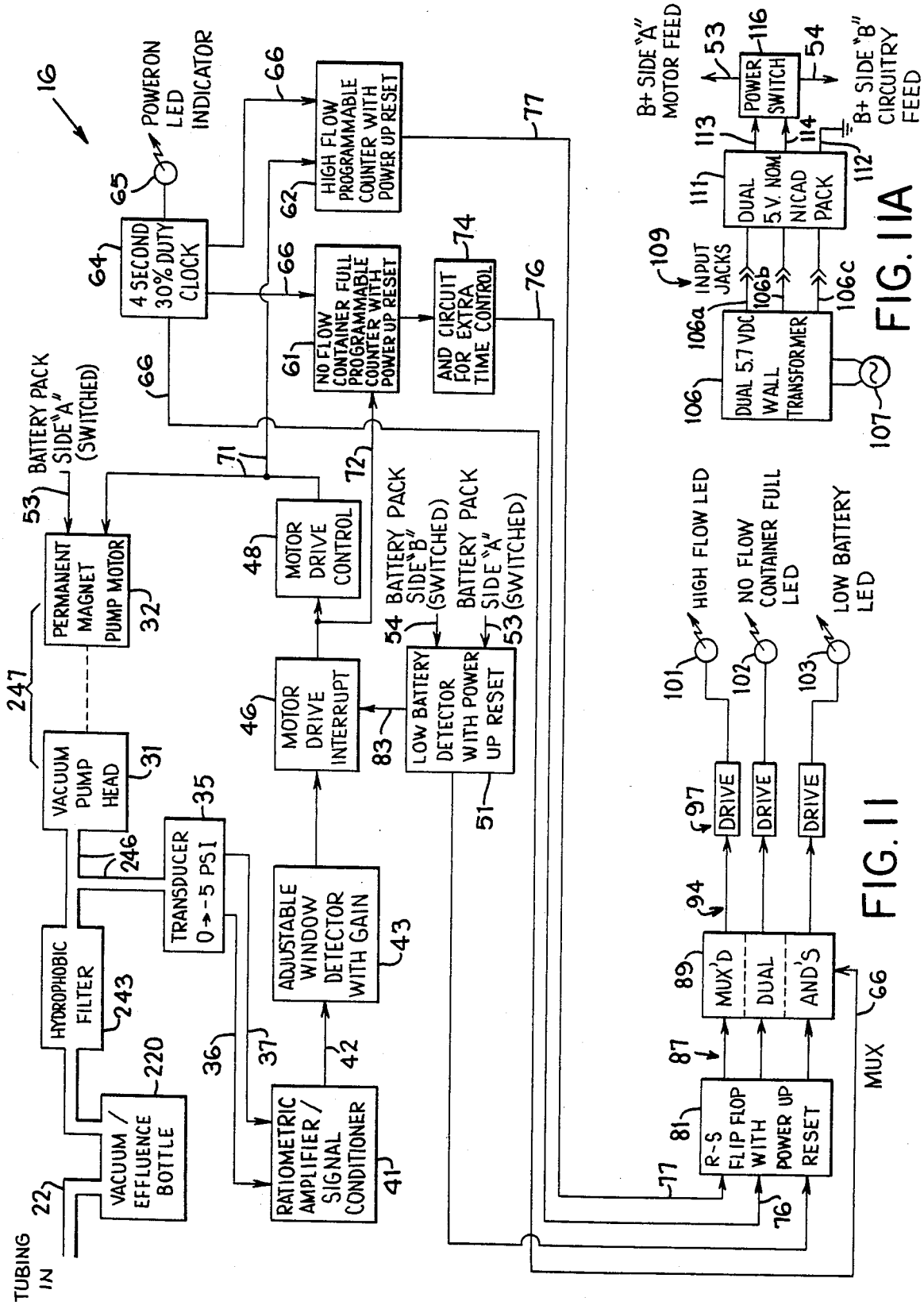
FIG. 11 is a block diagram of the control circuitry of the system of FIG. 1.
Figure 12:
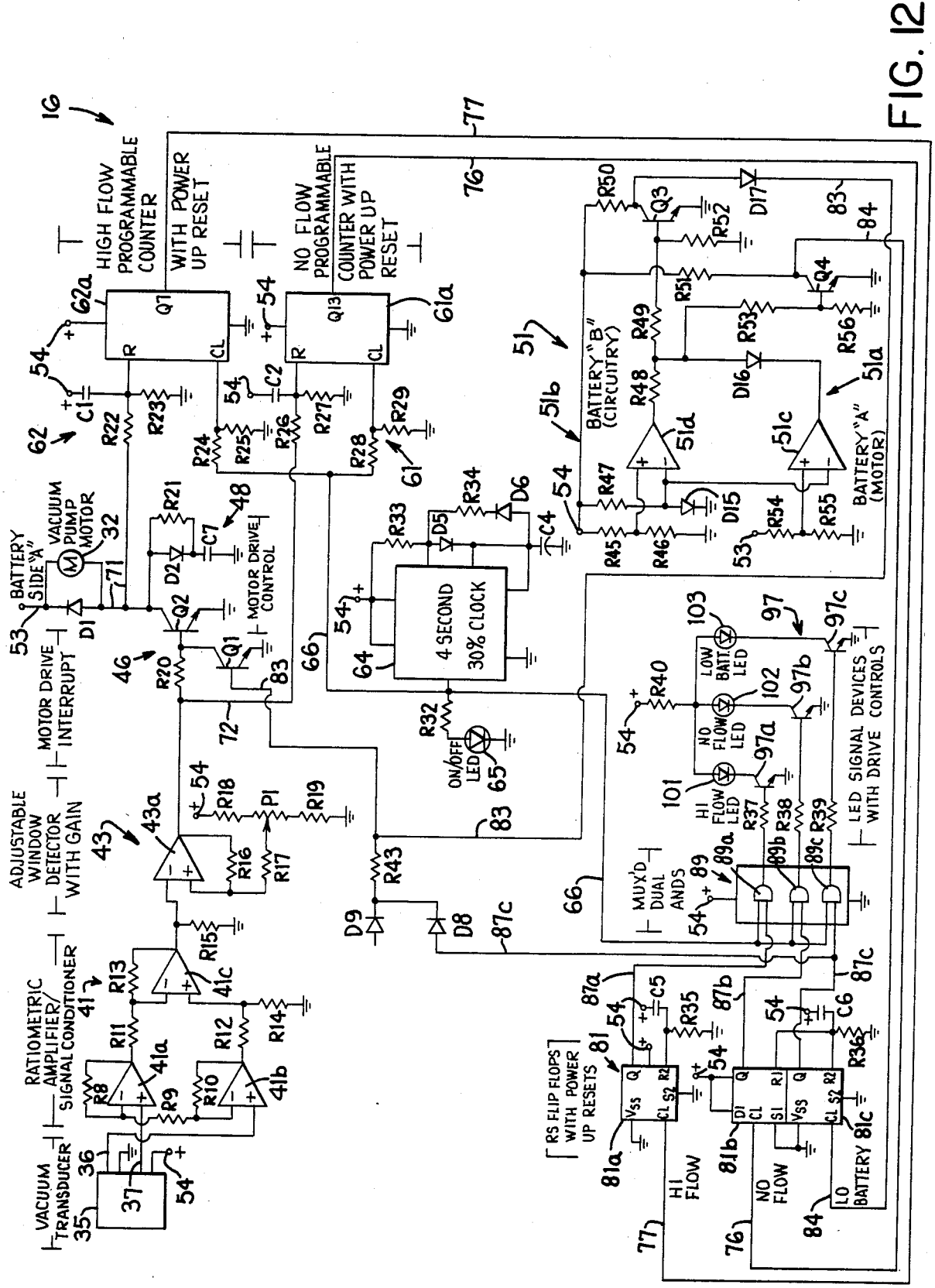
FIG. 12 is a circuit diagram corresponding in content to the block diagram of FIG. 11 and disclosing the control circuitry in more detail.

Control circuitry 16, hereafter described with respect to FIGS. 11 and 12, is contained within the housing 201, and for the most part, on a printed circuit board 316 (FIGS. 8 and 9) spaced in substantially parallel relation between the forward facing wall 210 and back wall 204 in the lower part of the housing 201. The printed circuit board 316 is fixed as by screws 317 to abutments 318 extending rearward from the forward facing wall 210 of the housing.

In addition, the aforementioned shelf assembly 241 carries additional components of the control circuitry 16, as hereafter further described. Such components include a potentiometer P1 (FIGS. 9 and 10), a battery pack 111 (FIGS. 8–10), and the aforementioned motor driven vacuum pump 247. The battery pack 111 here is a commercial 5 volt dual nickel-cadmium unit having plug-type terminals (not shown) in the bottom thereof receivable in socket terminals (not shown) in a rearward slidable shelf 319 through which protrude battery output conductors 112–114. If desired, the top of the cover 213 may include a door 213a (FIGS. 8 and 9) rearwardly slidable off the cover 213 for easier access to the potentiometer P1 and battery pack 111.

In addition, the front wall 203 (FIG. 1) of the housing carries visible indicators 65, 101, 102 and 103, hereafter described with respect to FIG. 11, and appropriate labeling.

Also, a multiple contact input jack 109 (FIG. 2) is provided in one side 208 of the housing 201 for applying recharging current to the battery pack 111. Internal electrical connections within the housing are not shown in FIGS. 1–10 but are instead shown in the circuitry drawings at FIGS. 11, 11A and 12, to which attention is now directed.

Operating electrical potential for the control circuitry 16 and the motor driven vacuum pump unit 247 is preferably provided by a commercially available converter 106 (FIG. 11A), having internal transformer and rectifier circuitry, and arranged to plug into a commercial power line outlet (in the United States for example a 120 volt, 60 cycle AC outlet) and to supply to the plug (not shown) of a conventional jack unit two low voltage (here for example 5.7 volts) lines 106a and 106b referred to a reference, or ground, line 106c, for plugging into the socket 109 of the jack connection carried, as above discussed, on the side of the housing, to supply the two sections of the dual battery pack 111. The battery pack 111 connects through a ground line 112 to the ground side of the control circuitry 16 (as indicated by the conventional ground symbols in FIG. 12). The two battery pack sections respectively connect through the positive DC supply lines 113 and 114 to corresponding sections 116A and 116B of power switch 116 and (when the latter is conductive) to the motor feed conductor 53 at side "A" of the FIG. 11 power supply and to circuitry feed conductor 54, at side "B" of the DC power supply. Thus, DC operating potential is applied to feed lines 53 and 54 only when the power switch 116 is rendered conductive by completion of insertion of the reservoir 13 into place on the base unit 12 discussed above with respect to FIGS. 3A and 8. Conversely, DC operating potential is removed from the lines 53 and 54 by removal of the reservoir from the housing.

The upper left portion of FIG. 11 schematically discloses the vacuum path with the reservoir 13 installed on the base unit 12, namely with negative pressure applied to the wound drain tube 22 through bottle 220, hydrophobic filter 243 and vacuum line 246 by the motor driven vacuum pump 247, here shown as a vacuum pump head 31 driven by a permanent magnet pump motor 32.

Referring to FIGS. 11 and 12, a conventional vacuum to electric transducer 35 has a vacuum inlet connected at a branch of the vacuum line 246. Transducer 35 has an effective range of, for example, 0 to −5 pounds per square inch (psi).

The vacuum transducer 35 has voltage output lines 36 and 37, the voltage level on one representing atmospheric pressure and the voltage level on the other representing pressure in the vacuum line 246, both voltage levels referred to circuit ground.

A ratiometric amplifier/signal conditioner unit 41 comprises a pair of input operational amplifiers 41a and 41b having noninverting inputs respectively driven by transducer output lines 37 and 36 and inverting inputs strapped together by a resistor R9 and to which are connected respective feedback resistors R8 and R10 from the respective outputs of the operational amplifiers 41a and 41b. Voltage outputs of the latter operational amplifiers are applied through respective resistors R11 and R12 to the inverting and noninverting inputs of a further operational amplifier 41c. Operational amplifier 41c has a feedback resistor R13 connected from its output to its inverting input and a bias resistor R14 connected from its noninverting input to ground. The operational amplifier 41c produces, across a grounded resistor R15, a voltage signal proportional to the pressure drop from atmospheric pressure to the negative pressure in vacuum line 246 and in bottle 220.

This vacuum, or negative pressure, signal is applied through a line 42 to an adjustable window detector 43, and more particularly to the inverting input of an operational amplifier 43a thereof. The gain of operational amplifier 43a is controlled by connecting its noninverting input to an output feedback resistor R16 and, through a resistor R17, to a voltage divider comprised of a resistor R18, potentiometer P1 and resistor R19 connected in series across the circuitry DC supply, from line 54 to ground. Adjustment of the potentiometer P1 changes both the width of the vacuum range, or "window", applied by the base unit 12 to the reservoir 13, and the amount by which such window (mostly the maximum negative pressure end of such window) is offset below atmospheric pressure. In one example according to the invention, the potentiometer P1 set at one extreme maintained the vacuum in the reservoir 13 between 1.5 and 4 negative psi and at its opposite extreme maintained the vacuum in the reservoir 13 at between 0.8 and 1.4 negative psi. The latter setting thus provides a relatively light vacuum which is permitted to fluctuate only over a relatively small range and is thus more suited for draining of a wound in relatively delicate tissue. On the other hand, the former setting provides a greater vacuum and permits wider fluctuation in vacuum and is thus more suited for wounds for example in heavy muscle tissue, if higher drainage rates are needed or if thicker and less flowable drainage liquids are encountered.

A motor drive control 48 comprises a transistor Q2 connected at its base through a resistor R20 from the output of window detector 43. The collector-emitter path of transistor Q2 connects in parallel with a series diode D2 and capacitor C7, the diode D2 being paralleled by resistor R21. A series path leads from battery side "A", namely the DC positive line 53, through the input terminals of vacuum pump motor 32 (paralleled by an inverse oriented diode D1) through the collector and emitter of transistor Q2 to ground, such that a high or low voltage out of the window detector 43 respectively causes the transistor Q2 to conduct through (and hence energize) motor 32 or block and thereby turn off the motor 32. The diode D2, resistor R21, and capacitor C7 minimize current to the transistor Q2 output by in effect shunting the oscillations of the back EMF of motor 32 through diode D1.

A motor drive interrupt unit 46 comprises a transistor Q1 connected between the base of transistor Q2 and ground and actuable to interrupt conduction of transistor Q2 through vacuum pump motor 32, upon application of a positive base potential to line 83 connected to the base of transistor Q1. The control circuitry 16 includes several condition monitoring units each responsive to occurrence of undesired, or fault, conditions for placing a high potential on line 83 and thereby disabling the vacuum pump motor 32.

For example, to monitor battery pack voltage, the control circuit 16 includes a low battery detector unit 51 comprising sections 51a and 51b respectively responsive to DC voltage lines 53 and 54. The detector sections 51a and 51b respectively include operational amplifiers 51c and 51d. It will be understood that all the operational amplifiers in FIG. 12 are conventionally supplied with DC operating potential by connections not shown to the positive DC circuitry feed line 54 and the ground line 112 of the battery pack. The noninverting input of operational amplifier 51c monitors the voltage of DC supply line 53 by connection intermediate the ends of a voltage divider comprising resistors R54 and R55 connected between line 53 and ground. Similarly, the noninverting terminal of operational amplifier 51d monitors the DC voltage line 54 by connection intermediate the ends of a voltage divider comprising resistors R45 and R46 connected between line 54 and ground. The inverting inputs of operational amplifiers 51c and 51d are supplied a reference potential defined by the constant forward voltage drop across a diode D15 connected in series with a current limiting resistor R47 running from DC voltage supply line 54 to ground. If the voltage applied to the noninverting inputs of operational amplifier 51c and 51d is less than the voltage drop across diode D15, due to the voltage on line 53 and 54 being at some higher though still inadequate level, the output of the corresponding operational amplifier 51c and 51d will be low.

A transistor Q3 connects in series with a current limiting resistor R50 from positive line 54 to ground and a bias resistor R52 connects its base to ground. A further transistor Q4 connects in series with a resistor R51 from positive line 54 to ground and a bias resistor R56 connects its base to ground. The bases of transistor Q3 and Q4 connect through respective resistors R49 and R53 and a common series resistor R48 to the output of operational amplifier 51d. Thus, inadequate DC circuit voltage on line 54 and hence a low output voltage from operational amplifier 51d turns off transistors Q3 and Q4. The resulting high positive collector voltages pass, respectively, through a diode D17 and line 83 to turn on the motor drive interrupt transistor Q1 and thus disable the vacuum pump motor 32, and through a low battery signal line 84 to change to a fault state one flip-flop 81c of a fault condition memory 81.

Back in the low battery detector 51, a clamping diode D16 connects the junction point of above-mentioned resistors R48, R49 and R53 to the output of operational amplifier 51c. Thus, inadequate DC motor voltage on line 53, resulting in low voltage output from operational amplifier 51c, acts through the diode D16 to again turn off both transistors Q3 and Q4 and apply high collector potential to their respective fault lines 83 and 84 to again turn off vacuum pump motor 32 and the change flip-flop 81c to a fault state. A voltage high, or fault signal, is thus applied to both lines 83 and 84 if either of the circuit and motor supply voltages on lines 54 and 53 are insufficient. In contrast, if both voltages are sufficient, then the bases of transistors Q3 and Q4 are high and fault lines 83 and 84 are low, indicating no fault and failing to either change the flip-flop 81c to a fault state or to disable vacuum pump motor 32.

Note that regardless of whether the motor supply voltage on line 53 is sufficient or not, an insufficient circuit supply voltage on line 54 results in low battery detector 51 applying the high potential fault signal to lines 83 and 84. On the other hand, the circuit 51 permits the fault lines 83 and 84 to remain at a low potential, namely a non-fault condition, only when both of the DC supply lines 53 and 54 are at adequate potential.

If the circuitry supply voltage 54 is zero or near zero, in other words so low that an adequate positive fault potential cannot be established on lines 83 and 84, the output of the window detector 43 will necessarily be too low to turn on motor drive control transistor Q2, such that the vacuum pump will not operate even if the motor supply voltage 53 is adequate. The high fault voltages on lines 83 and 84 will thus be understood to occur when the voltages on supply lines 53 and 54 are above zero but below the desired minimum operating potential, so as to insure disabling of the vacuum pump before dropping battery voltage can introduce error into the operation of the control circuit 16 or appreciably slow the vacuum pump motor 32.

When a low battery condition changes flip-flop 81c to a fault state, the Q output of the latter switches a line 87c to a high potential and holds that high potential even if the low battery condition improves somehow and the high potential fault signal on line 83 disappears. The high potential on line 87c is applied through a diode D8 and resistor R43 and line 83 to the base of motor interrupt transistor Q1 to continue disabling the vacuum pump motor 32, until such time as the flip-flop 81C may be reset by an attendant as described hereinafter.

The control circuitry 16 includes further monitoring units 62 and 61 for indicating respectively that the pump motor 32 has run continuously for too long a time (characterized as a "high flow" condition) and for indicating that the pump motor 32 has run for an abnormally short period of time (characterized as a "no flow" condition). The high flow fault condition exists when the pump motor 32 runs for an excessive time without achieving the maximum negative pressure in the bottle 220 set by the window detector 43. Such may be caused by, for example, a break in the drain tube 22 or dislodgment of the remote end of the drain tube 22 from the wound, to in effect vent the bottle 220 to the atmosphere. On the other hand, the no flow fault condition occurs when the vacuum pump very quickly pulls the maximum negative pressure in the bottle 220 set by of window detector 43, which may, for example, be caused by blockage of flow through the tube 22, as by plugging or crushing of the tube. Monitoring units 62 and 61 include corresponding timing means, here programmable counters 62a and 61a having respective reset inputs R connected through corresponding resistors R22 and R26 and lines 71 and 72 respectively to the collector of motor drive control transistor Q2 and to the output of adjustable window detector 43.

Thus, appearance of a low potential on the reset input R of either counter starts it counting. High flow counter 62a thus starts counting upon turning on of vacuum pump motor 32 by transistor Q2 and no flow counter 61a starts counting when the output of window detector 43 swings low to turn off transistor Q2 and motor 32.

For example, if when started, the vacuum pump motor 32 promptly establishes maximum desired negative pressure in the bottle 220, the window detector 43 shuts off transistor Q2 and motor 32, and the line 71 goes high to reset the counter 62a prior to completion of its count.

In the same way, if with the pump motor 32 off the vacuum in the bottle 220 diminishes at a sufficient rate, due to proper drawing of liquid from the wound through tube 22, the window detector 43 turns on transistor Q2 and motor 32, and the line 72 goes high to reset low flow counter 61a prior to completion of its count.

A conventional clock source 64 provides clock pulses at 4-second intervals on a clock line 66 and then, by means of corresponding resistor voltage dividers R24, R25 and R28, R29, to the respective clock inputs of high flow counter 62a and low flow counter 61a to advance such counters at the clock rate when the respective reset inputs R thereof are low as above described. The counters 61a and 62a are conventionally presettable as to the count level at which they will provide an output (here a high) on their respective output terminals Q13 and Q7 and hence on their respective output lines 76 and 77.

Such an end of count, or high, signal on either line 76 or 77 is applied to the clock input of a corresponding RS flip-flop 81b or 81a (of the RS flip-flop unit 81) which switches the respective Q output high indicating a respective no flow or high flow fault condition has occurred. Each of the flip-flops 81a, 81b and 81c thus acts as a memory device for maintaining its corresponding Q output line 87a, 87b or 87c high regardless of any subsequent change in the potential on its corresponding clock input line 77, 76 or 84.

Corresponding high flow, no flow and low battery indicators 101, 102 and 103 are driven by the Q output lines 87a, 87b and 87c respectively when high, namely when a high flow, no flow or low battery fault condition exists. More particularly, each indicator 101, 102 and 103 connects in series from the circuit positive DC supply 54 through a common resistor R40 to the collector-emitter circuit of a corresponding transistor 97a, 97b and 97c actuable at its base by a high DC voltage through corresponding current limiting resistors R37, R38 and R39 from the output of a corresponding AND gate 89a, 89b and 89c. The AND gates 89 have respective first inputs connected to the flip-flop Q output lines 87a, 87b and 87c. The second inputs of the AND gates 89 commonly connect to the clock output line 66 from the 4-second clock 64 above described. Preferably the clock 64 has a relatively low duty cycle, or conductive time (for example 30%) to reduce the load on the battery pack 111. Thus, upon occurrence of a high flow, no flow or low battery condition, the resulting high potential on the corresponding flip-flop Q output line 87a, 87b or 87c acts through the corresponding one of the AND gates 89, which is enabled by the clock once every 4 seconds, for 30% of its 4-second interval to turn on the corresponding transistor 97a, 97b or 97c and hence the corresponding indicator 101, 102 or 103, which thus flashes on at the same rate and for the same duration, to warn hospital personnel of the fault condition. To minimize battery drain, indicators 101, 102 and 103 are preferably light emitting diodes (LEDs).

To indicate that operating potential is supplied through line 54 to the control circuitry 16, an on/off indicator 65 (preferably an LED) is driven through a resistor R32 from the clock output line 66 to flash in the 4-second, 30% duty cycle sequence above discussed. The timing of the clock 64 is controlled by conventional timing circuitry here included in the external connection of resistors R33 and R34, diodes D5 and D6 and capacitor C4 as shown in FIG. 12. If desired, a different clock pulse rate and a different duty cycle may be selected.

In the embodiment shown, a diode D9 connects through aforementioned resistor R43 to the base of motor drive interrupt transistor Q1 and provides, at its anode, a test point, to which application of a positive potential will cause the motor drive interrupt transistor Q1 to disable the vacuum pump motor 32.

In the embodiment shown, power up reset connections are provided for the counters and flip-flops. More particularly, a series capacitor C1 and resistor R23 connects between circuitry positive supply 54 and ground with the high flow counter 62a having its reset input connected intermediate such capacitor and resistor, such that a rise from zero to normal operating potential of the line 54, by turning on the power switch 116 (FIG. 11) applies a positive pulse through the capacitor C1 to the reset terminal R which resets the counter to zero.

Series capacitor C2 and resistor R27 provide a similar power up reset for no flow counter 61a. Similar series capacitor C5 and resistor R35 and similar series capacitor C6 and resistor R36 provide for power up reset of the flip-flops 89, thus restoring the Q output lines thereof to their normal low condition.

Figure 7A:
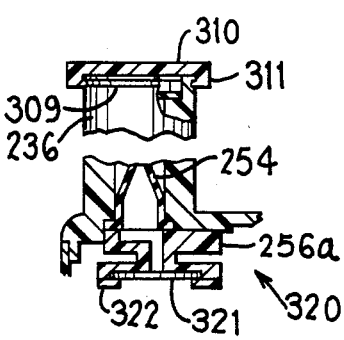
FIG. 7A discloses a modification of the vacuum connection assembly boss portion of the receptacle of FIG. 7.

As seen in the lower portion of FIG. 7A, the float valve assembly 256–260 of FIG. 7 may be replaced by a hydrophobic filter unit 320 in which a modified retainer 256a supports a conventional hydrophobic filter element 321 at the bottom thereof by a fixed annular shelf 322 for permitting gas flow but blocking liquid flow through its internal passage 323 between the one-way valve 254 and the interior of the bottle 220. Unit 320 blocks liquid from leaving the bottle even if the latter is tilted or inverted or agitated, as well as when the bottle is full of liquid. The cap 310 is largely redundant if the unit 320 is used, except perhaps to keep the top of the boss 236 and membrane 251 clean.

The reservoir 13 is preferably of transparent or translucent plastic material. Thus, the interior liquid level can be seen and measured on a volume scale (FIG. 1) on the side of the bottle. A visual determination of whether the bottle interior is at a negative pressure can be made by observing the shape of a resilient member communicating with the interior of the bottle. Here, as seen through the wall 236, the profile of the duckbill valve 254 flattens when the bottle interior is at a negative pressure.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property of privilege is claimed are defined as follows:

1. A continuous vacuum drainage system for wound drainage, comprising:
   a drain reservoir;
   a base unit including means for releasably attaching thereto said drain reservoir and having means responsive to releasable attachment thereto of said drain reservoir for evacuating said drain reservoir at a subatmospheric pressure in a predetermined range, said drain reservoir having means continuously operable before, during and after release from said base unit for uninterrupted suction draining of a wound into said drain reservoir.

2. The apparatus of claim 1 in which said reservoir includes a vacuum port with seal means normally closed to maintain a subatmospheric pressure in said reservoir for suction draining of a wound while said reservoir is detached from said base unit, said base unit having a vacuum pump and means releasably connecting said vacuum port with said vacuum pump for actuating said vacuum pump and opening said seal means and thereby for suction draining a wound while said reservoir is mounted on said base unit.

3. A continuous vacuum drainage system for wound drainage on a patient, comprising:
   a base unit having a vacuum source;
   means defining a portable drain reservoir bottle alternately (1) engageable on said base unit for charging to a subatmospheric pressure and (2) carriable with the patient to locations remote from a base unit while still at subatmospheric pressure, said drain reservoir bottle having a drain port for connection of said bottle to a wound to be drained for suction draining of wounds with said bottle both (1) engaged with said base unit and (2) located remote from said base unit, said bottle having a vacuum port with seal means for sealing the drain reservoir bottle, said seal means being normally closed while said drain reservoir bottle is at subatmospheric pressure and remote from said base unit;
   means on said base unit for opening said seal means with said bottle engaged on said base unit and said vacuum port connected to said vacuum source for said charging of said base to subatmospheric pressure.

4. The system of claim 3 in which said vacuum source includes in series a hydrophobic filter means in said base unit capable of passing gasses but not liquids to said vacuum source, said seal means comprising an annular resilient seal member and said opening means comprising a hollow stem associated with said base unit and sealingly insertable through said annular seal member, valve means on said reservoir bottle for permitting withdrawal of gasses from said reservoir bottle by said vacuum source in said base unit through said stem and hydrophobic filter means but sealing against flow of fluids back into said reservoir bottle, and means in said reservoir bottle for preventing against drawing of liquid from said reservoir therethrough into said vacuum source in the event of a rise in liquid level within said reservoir bottle toward said vacuum connection.

5. The apparatus of claim 4 in which said base unit includes a pocket and said reservoir bottle includes a boss extending therefrom for insertion into said pocket, said hydrophobic filter means comprising a hydrophobic filter disposed within said base unit, said preventing means being a float valve, said hollow stem extending from said hydrophobic filter means into said pocket, said annular seal member being an annular latex membrane, said valve means being a one-way valve means, said annular latex membrane, one-way valve means and float valve being sequentially located inboard from the end of said boss, such that said hollow stem is receivable through said membrane when said boss is fully inserted into said pocket in said base unit.

6. The system of claim 4 including a boss protruding from said reservoir bottle for releasable reception in a pocket in said housing, a cap fitted to the end of said boss and applicable thereto for causing same when said reservoir bottle is not connected with said base unit, and including connector means on said cap and boss for releasably connecting same.

7. The system of claim 3 in which said reservoir includes a bottom emptying port, said bottom emptying port having valve means manually openable for draining said reservoir bottle, said valve means being removable from said bottom emptying port to permit maximum width communication between the interior of said reservoir bottle and the atmosphere.

8. The system of claim 3 in which said base unit includes removable back and top portions remote from the portion of the base unit to which the reservoir bottle is attachable.

9. The system of claim 3 including means secured to said housing for releasably supporting same on a patient support or the like.

10. The system of claim 3 including control means responsive to predetermined conditions in said reservoir bottle for energizing said vacuum source, said base unit comprising a housing, said control means being contained in said housing, said housing including circuit board support means, said housing further including shelf means therein for supporting said vacuum source, a voltage source for said control means, said bottle having top and back sides, said housing in elevation having a substantially inverted L-shape defining a downwardly and forwardly opening recess for receiving the top and back sides of the reservoir bottle, said vacuum source connecting into said recess, a forward facing wall of said recess including means adapted to guide said bottle into properly received relation with said housing, said shelf means being disposed in a horizontal upper leg of said L-shaped housing, said printed circuit board support means being disposed in a depending leg of the L-shaped housing, and including switch means adjacent the front face of said housing and adjacent said printed circuit board mounting means for sensing the insertion of a reservoir bottle into coactive relation with said housing.

11. A continuous vacuum drainage system for wound drainage on a patient, comprising:
a base unit;
a portable drain reservoir carriable by the patient or a mobile patient support to locations remote from said base unit, said drain reservoir comprising a portable bottle having a drain port for connection of said bottle to a wound to be drained and a vacuum port connectible to a vacuum source for reducing pressure in said bottle;
said base unit comprising a housing to which said reservoir is releasably attachable and a vacuum source in said housing; and
interengaging means on said reservoir and housing including (1) mounting means for releasable attachment of said reservoir on said housing and (2) vacuum connection means for connecting said vacuum source to said vacuum port,
said housing including recess means for receiving said reservoir vertically thereinto, said vacuum connection means being located at said recess means of said housing and on the portion of said reservoir receivable in said recess means, such that insertion of said reservoir into said recess means of said housing substantially simultaneously interconnects said guide means and vacuum connection means of said housing and reservoir in a single motion, said wound drain port being located on the top portion of said reservoir in an area thereof outside said housing recess, said reservoir having an emptying port in an area thereof outside said housing recess.

12. The system of claim 11 including a substantially L-shaped deflectable member extending from said reservoir in the direction of said single motion insertion and means defining an undercut opening in said housing for receiving said L-shaped member and including a ledge on said housing, which ledge has a camming surface for deflecting the entering deflectable member and a retaining surface engageable by said L-shaped member for positively holding said reservoir against removal from said housing, said opening including a first portion into which said L-shaped member is insertable and a second portion accessible from outside said housing for disengaging said L-shaped member from said retaining surface and removal of said reservoir from said housing.

13. The system of claim 11 in which said vacuum connection means includes a boss extending from said reservoir in said direction of single motion insertion and an opposing pocket in said housing for receiving said boss, said pocket having taper-ended guide means for guiding said boss coaxially into said pocket to effect said vacuum connection.

14. A continuous vacuum drainage system for wound drainage on a patient, comprising:
a base unit;
a portable drain reservoir carriable by the patient or a mobile patient support to locations remote from said base unit, said drain reservoir comprising a portable bottle having a drain port for connection of said bottle to a wound to be drained and a vacuum port connectible to a vacuum source for reducing pressure in said bottle;
said base unit comprising a housing to which said reservoir is releasably attachable and a said vacuum source in said housing; and
interengaging means on said reservoir and housing including (1) mounting means for releasable attachment of said reservoir on said housing and (2) vacuum connection means for connecting said vacuum source to said vacuum port;
said wound drain port comprising a one-way valve oriented to permit in-flow of drainage liquid from a wound but preventing transfer of fluid out of said reservoir back to said wound,
said wound drain port includes a boss protruding from said reservoir adjacent the upper end thereof, and including a wound drainage hose terminated in means snugly receivable in telescoped relation with said boss, said snugly receivable means and boss having an L-shaped slot in the free end of one thereof coactive with a pin on the other thereof for effecting releasable locking of said hose on said reservoir, said drain port having a recess at the inner end of the boss to receive the flanged end of said one-way valve and means bearing on said flanged end of said one-way valve to hold the latter in said recess at the inner end of said boss, said boss having a central through-bore for passing of wound drainage liquid from said hose into the interior of said reservoir.

15. The apparatus of claim 14 including lug means protruding from reservoir adjacent said boss, one of said boss and lug means having an indentation for receiving in snap-fit relation fastener means for securing and supporting said reservoir on a patient or patient support independent of said housing.

16. A continuous vacuum drainage system for wound drainage, comprising:
a drain reservoir placeable at negative pressure to receive drainage from the wound;
a motor driven vacuum pump and means for effecting a connection of said pump with said drain reservoir for applying said negative pressure thereto;
control means for controlling said vacuum pump;
a power source for energizing said vacuum pump and control means;
said control means comprising window detector means having both a high negative pressure threshold and low negative pressure threshold and being responsive to a negative pressure input below said low negative pressure threshold for turning on said vacuum pump and responsive to a negative pressure input above said high negative pressure threshold for turning off said vacuum pump, said window detector means being operatively interposed between said power source and said motor driven vacuum pump for so turning the pump on and off such that the pressure in said connection ranges freely and automatically between said high and low negative pressure thresholds, and means responsive to the pressure in the connection between said reservoir and pump for supplying the negative pressure input to the window detector means.

17. A continuous vacuum drainage system for wound drainage, comprising:
a drain reservoir placeable at negative pressure to receive drainage from the wound;
a motor driven vacuum pump releasably connected with said drain reservoir for applying said negative pressure thereto;
control means for controlling said vacuum pump;
a power source for energizing said vacuum pump and control means;
said control means comprising motor drive control means interposed between said power source and said motor driven vacuum pump, and means responsive to the pressure in said reservoir and operatively connected to said motor drive control means for maintaining the pressure in said reservoir within a preselected negative pressure range; and
a base unit containing said pump, control means and power source and to which said drain reservoir is releasably engaged, said control means including power switch means responsive to withdrawal of said reservoir from said base unit for shutting off said pump.

18. A continuous vacuum drainage system for wound drainage, comprising:
a drain reservoir placeable at negative pressure to receive drainage from the wound;
a motor driven vacuum pump connected with said drain reservoir for applying said negative pressure thereto;
control means for controlling said vacuum pump;
a power source for energizing said vacuum pump and control means;
said control means comprising motor drive control means interposed between said power source and said motor driven vacuum pump, and means responsive to the pressure in said reservoir and operatively connected to said motor drive control means for maintaining the pressure in said reservoir within a preselected negative pressure range, said power source being a battery, said control means further including battery level detector means connected to said motor drive control means and responsive to a battery charge level below a desired minimum for causing same to shut off said pump.

19. The system of claim 18 in which said battery comprises a pump voltage source and a circuitry voltage source, said battery level detector means having first and second detectors respectively monitoring said pump voltage source and circuitry voltage source.

20. The system of claim 19 in which said control means includes low battery monitor means including indicator means and responsive to insufficient charge level at least in at least one said voltage source for actuating said indicator means and interrupting energization of said pump.

21. A continuous vacuum drainage system for wound drainage, comprising:
a drain reservoir placeable at negative pressure to receive drainage from the wound;
a motor driven vacuum pump and means for connecting same with said drain reservoir for applying said negative pressure thereto;
control means for controlling said vacuum pump;
a power source for energizing said vacuum pump and control means;
said control means comprising motor drive control means interposed between said power source and said motor driven vacuum pump, and means responsive to the pressure in said reservoir and operatively connected to said motor drive control means for maintaining the pressure in said reservoir within a preselected negative pressure range, said control means further including high flow monitor means including indicator means and counter means responsive to running of said vacuum pump for an excessive time for actuating said indicator means.

22. A continuous vacuum drainage system for wound drainage, comprising:
a drain reservoir placeable at negative pressure to receive drainage from the wound;
a motor driven vacuum pump and means for connecting same with said drain reservoir for applying said negative pressure thereto;
control means for controlling said vacuum pump;
a power source for energizing said vacuum pump and control means;
said control means comprising motor drive control means interposed between said power source and said motor driven vacuum pump, and means responsive to the pressure in said reservoir and operatively connected to said motor drive control means for maintaining the pressure in said reservoir within a preselected negative pressure range, said control means further including low flow monitor means including indicator means and counter means responsive to running of said vacuum pump for an insufficient time for actuating said indicator means.

23. A continuous vacuum drainage system for wound drainage, comprising:
a drain reservoir placeable at negative pressure to receive drainage from the wound;
a motor driven vacuum pump and means for connecting same with said drain reservoir for applying said negative pressure thereto;
control means for controlling said vacuum pump;
a power source for energizing said vacuum pump and control means;
said control means comprising motor drive control means interposed between said power source and said motor driven vacuum pump, and means responsive to the pressure in said reservoir and operatively connected to said motor drive control means for maintaining the pressure in said reservoir within a preselected negative pressure range, said power source comprising a battery, said control means further including indicator means and monitor means responsive to at least one of a low battery charge level, a too long pump run time, or a too short pump run time, for actuating said indicator means, said monitor means including flip-flop means responsive to actuation of a said indicator means for maintaining said indicator means actuated.

24. The system of claim 23 in which said control means includes a clock pulse source and AND-gate means connected between said flip-flop means and indicator means, said AND-gate means being briefly and repetitively enabled by said clock pulse source, said clock pulse source having less than a 50 percent "on" duty cycle to conserve battery charge.

25. The system of claim 23 including a base unit incorporating said power source and said control means and said vacuum pump, said control means comprising means responsive to connection of said reservoir to said base unit for connecting said power source to said vacuum pump and control means, said control means incorporating further indicator means driven by said clock pulse source for indicating said reservoir is connected to said base unit.

26. A continuous vacuum drainage system for wound drainage on a patient, comprising:
a base unit;
a portable drain reservoir carriable by the patient or a mobile patient support to locations remote from said base unit, said drain reservoir comprising a portable bottle having a drain port for connection of said bottle to a wound to be drained and a vacuum port connectible to a vacuum source for reducing pressure in said bottle;
said base unit comprising a housing to which said reservoir is releasably attached and a vacuum source in said housing; and
interengaging means on said reservoir and housing including (1) mounting means for releasable attachment of said reservoir on said housing and (2) vacuum connection means for connecting said vacuum source to said vacuum port, in which said vacuum connection means on said reservoir includes a one-way valve means aimed to permit withdrawal of gases from said reservoir but preventing fluid flow therethrough back into said reservoir, and further includes a hydrophobic filter in series between said one-way valve means and the interior of said reservoir for passing gases but preventing escape of liquid from said reservoir to said one-way valve.

27. The apparatus of claim 26 including a hollow boss projecting from the top portion of the reservoir, and having an inner end communicating with the interior of the reservoir and an outer end receivable releasably in a recess in said base unit, said hydrophobic filter being located at said inner end of said boss and facing into the interior of said reservoir, said one-way valve means being located in and intermediate the ends of said boss.

28. A continuous vacuum drainage system for wound drainage on a patient, comprising:
a base unit;
a portable drain reservoir carriable by the patient or a mobile patient support to locations remote from said base unit, said drain reservoir comprising a portable bottle having a drain port for connection of said bottle to a wound to be drained and a vacuum port connectible to a vacuum source for reducing pressure in said bottle;
said base unit comprising a housing to which said reservoir is releasably attached and a vacuum source in said housing; and
interengaging means on said reservoir and housing including (1) mounting means for releasable attachment of said reservoir on said housing and (2) vacuum connection means for connecting said vacuum source to said vacuum port;
means on said reservoir defining a resiliently flexible wall having one side thereof facing into said reservoir and the oppste side thereof facing outward of said drain reservoir, said flexible wall being visible from outside said drain reservoir, said wall having a first shape with no pressure drop thereacross and a second and visibly different shape when said drain reservoir is evacuated for indicating that the interior of the reservoir is at a negative pressure.

29. A continuous vacuum drainage system for wound drainage on a patient, comprising:
a base unit;
a portable drain reservoir carriable with the patient to locations remote from said base unit, said drain reservoir having a drain port for connection to a wound to be drained and a vacuum port;
said base unit comprising a housing on which said reservoir is releasably engaged and a vacuum source in said housing thereby engaged with said vacuum port of said reservoir; and
interengaging means on said reservoir and housing actuable in response to said engagement of said reservoir on said housing and vacuum sensing means actuable in response to reservoir, said one-way valve means being located in and intermediate the ends of said boss.

30. The system of claim 29 in which said interengaging means includes power switch means on said housing positioned for actuation by said releasable attachment of said reservoir onto said base unit, and control means in said housing enabled by said actuation of said power switch means and responsive to sensing of predetermined conditions in said reservoir by said vacuum sensing means for energizing said vacuum source.

31. The system of claim 30 including protruding means fixed on said reservoir coactive with an actuator of said switch means on said housing for actuating said switch upon insertion of said reservoir into recess means on said housing, in which said actuator faces into said recess means and said protruding means on said reservoir are on a face of said reservoir received in said recess means.

32. The system of claim 31 in which said recess means comprises first and second recesses on said housing receiving different parts of said reservoir therein.

* * * * *

UNITED STATES PATENT AND TRADEMARK OFFICE
CERTIFICATE OF CORRECTION

PATENT NO. : 4 569 674

DATED : February 11, 1986

INVENTOR(S) : Earl G. PHILLIPS et al

It is certified that error appears in the above-identified patent and that said Letters Patent is hereby corrected as shown below:

Please cancel Claim 29, lines 34 - 49, and replace with the following:

---29. A continuous vacuum drainage system for wound drainage on a patient, comprising:

a base unit;

a portable drain reservoir carriable with the patient to locations remote from said base unit, said drain reservoir having a drain port for connection to a wound to be drained and a vacuum port;

said base unit comprising a housing on which said reservoir is releasably engaged and a vacuum source in said housing thereby engaged with said vacuum port of said reservoir; and

UNITED STATES PATENT AND TRADEMARK OFFICE
CERTIFICATE OF CORRECTION

PATENT NO. : 4 569 674

DATED : February 11, 1986

INVENTOR(S) : Earl G. PHILLIPS et al

It is certified that error appears in the above-identified patent and that said Letters Patent is hereby corrected as shown below:

interengaging means on said reservoir and housing actuable in response to said engagement of said reservoir on said housing and vacuum sensing means actuable in response to an insufficient vacuum at said vacuum port for together causing said vacuum source to reduce the pressure in said reservoir, said interengaging means and vacuum sensing means being cooperably connected such that actuation of either alone is insufficient to cause said vacuum source to reduce the pressure in said reservoir.---.

Signed and Sealed this

Sixteenth Day of December, 1986

Attest:

DONALD J. QUIGG

Attesting Officer

Commissioner of Patents and Trademarks